(12) United States Patent
Shibuya et al.

(10) Patent No.: US 8,086,422 B2
(45) Date of Patent: Dec. 27, 2011

(54) METHOD FOR ANALYZING DEFECT DATA AND INSPECTION APPARATUS AND REVIEW SYSTEM

(75) Inventors: Hisae Shibuya, Yokohama (JP); Yuji Takagi, Kamakura (JP)

(73) Assignees: Hitachi, Ltd., Tokyo (JP); Hitachi High-Technologies Corporation, Tokyo (JP)

( * ) Notice: Subject to any disclaimer, the term of this patent is extended or adjusted under 35 U.S.C. 154(b) by 135 days.

(21) Appl. No.: 12/341,657

(22) Filed: Dec. 22, 2008

(65) Prior Publication Data

US 2009/0105990 A1 Apr. 23, 2009

Related U.S. Application Data

(60) Division of application No. 11/472,399, filed on Jun. 22, 2006, now abandoned, which is a continuation of application No. 11/095,614, filed on Apr. 1, 2005, now Pat. No. 7,084,968, which is a continuation of application No. 10/119,018, filed on Apr. 10, 2002, now Pat. No. 6,876,445.

(30) Foreign Application Priority Data

| Apr. 10, 2001 | (JP) | 2001-110794 |
| Jun. 8, 2001 | (JP) | 2001-173411 |
| Sep. 26, 2001 | (JP) | 2001-292786 |

(51) Int. Cl.
*G06F 11/00* (2006.01)

(52) U.S. Cl. .............. 702/183

(58) Field of Classification Search .......... 702/58, 702/59, 69, 90, 118, 137, 150, 179, 183, 702/185; 716/4; 324/718
See application file for complete search history.

(56) References Cited

U.S. PATENT DOCUMENTS

| 5,240,866 | A | | 8/1993 | Friedman et al. |
| 5,479,252 | A | | 12/1995 | Worster |
| 5,831,865 | A | * | 11/1998 | Berezin et al. ............ 716/7 |
| 5,943,437 | A | | 8/1999 | Sumie |
| 5,982,920 | A | * | 11/1999 | Tobin et al. ............ 382/145 |
| 6,097,887 | A | | 8/2000 | Hardikar et al. |
| 6,317,859 | B1 | * | 11/2001 | Papadopoulou ............ 716/4 |
| 6,466,895 | B1 | * | 10/2002 | Harvey et al. ............ 702/181 |
| 6,507,933 | B1 | * | 1/2003 | Kirsch et al. ............ 716/4 |
| 6,876,445 | B2 | * | 4/2005 | Shibuya et al. ............ 356/237.2 |
| 2002/0121915 | A1 | * | 9/2002 | Alonso Montull et al. ... 324/765 |

FOREIGN PATENT DOCUMENTS

| JP | 6-061314 | 3/1994 |
| JP | 10-214866 | 8/1998 |
| JP | 2000 222033 | 8/2000 |
| JP | 2000 332071 | 11/2000 |

* cited by examiner

*Primary Examiner* — Mohamed Charioui
(74) *Attorney, Agent, or Firm* — Antonelli, Terry, Stout & Kraus, LLP.

(57) ABSTRACT

The distribution states of defects are analyzed on the basis of the coordinates of defects detected by an inspection apparatus to classify them into a distribution feature category, or any one of repetitive defect, congestion defect, linear distribution defect, ring/lump distribution defect and random defect. In the manufacturing process for semiconductor substrates, defect distribution states are analyzed on the basis of defect data detected by an inspection apparatus, thereby specifying the cause of defect in apparatus or process.

22 Claims, 12 Drawing Sheets xy PLANE

θp PLANE

FIG. 6A
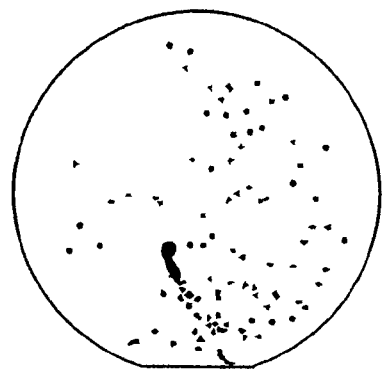
FIG. 6B
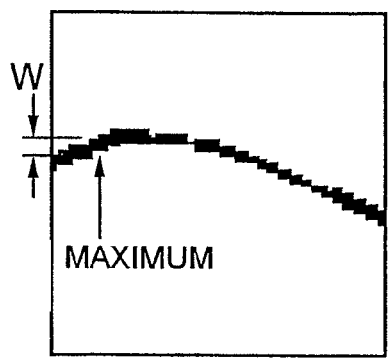
FIG. 6C  FIG. 6D  FIG. 6E  FIG. 6F
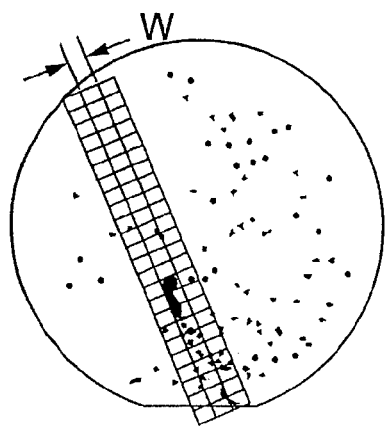   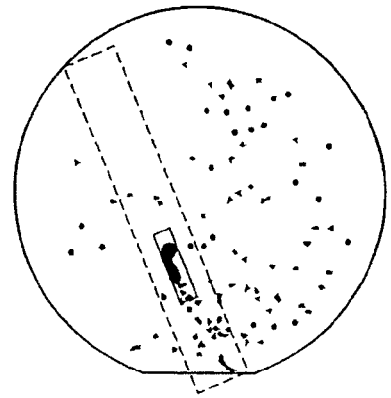

METHOD FOR ANALYZING DEFECT DATA AND INSPECTION APPARATUS AND REVIEW SYSTEM

CROSS REFERENCE TO RELATED APPLICATION

This application is a divisional Application of U.S. application Ser. No. 11/472,399, filed Jun. 22, 2006, now abandoned which, in turn, is a continuation of U.S. Ser. No. 11/095,614, filed Apr. 1, 2005 (now U.S. Pat. No. 7,084,968), which is a continuation of U.S. Ser. No. 10/119,018, filed Apr. 10, 2002 (now U.S. Pat. No. 6,876,445). The present case is also related to Ser. No. 11/472,368 which is also a continuation of Ser. No. 11/095,614, and which was filed on Jun. 22, 2006. The entire contents of all of these applications are incorporated herein by reference.

BACKGROUND OF THE INVENTION

The present invention relates to a defect data analyzing method for analyzing defect distribution states from the defect data detected by inspection apparatus in a semiconductor device manufacturing process in which circuit patterns are formed on a semiconductor substrate.

In the semiconductor device manufacturing process in which circuit patterns are formed on a semiconductor substrate (hereafter, referred to as semiconductor substrate production process), pattern defect inspection or foreign matter inspection is executed after each process, and the inspection results are analyzed, in order to improve and stabilize the yield. In other words, the operator observes the detected defects on an optical microscope or scanning electron microscope to know the kinds of the defects and identify the causes of the defects. This operation is called review. A method for making effective review is disclosed in JP-A-10-214866. In this method, the region in which defects are concentrated is recognized as a cluster from the defect distribution, and a review point is selected on the basis of the area and shape of the cluster.

Another method for analyzing the inspection result is proposed to try to estimate the cause of defects in apparatus or process from the analysis of defect distribution states. JP-A-6-61314 describes that wafers are grouped according to the state in which the defect map has clusters, and it is decided if they have similarities to known patterns, thereby identifying the cause of defects. In addition, U.S. Pat. No. 5,982,920 describes that each defect is classified as one of minute cluster, linear cluster, indefinite-form cluster and global type other than cluster, and related to a cause of defect.

SUMMARY OF THE INVENTION

It is an object of the invention to provide a defect data analyzing method capable of extracting a relatively high-density region even if the detected defects have a low-density distribution.

It is another object of the invention to provide a defect data analyzing method capable of fast classifying clusters of high-density regions of detected defects at a practical level.

The method described in the above-given JP-A-10-214866 needs to understand the cluster and then specify the shape. Therefore, it cannot be used for the distribution that is so thin that the cluster cannot be recognized. The method disclosed in the above JP-A-6-61314 or U.S. Pat. No. 5,982,920 also similarly requires to recognize the cluster, and thus cannot be used for thin defect distributions. However, in order to early detect an abnormal state of apparatus or process, it is necessary to be capable of treating such thin defect distributions.

In addition, according to the method described in the above JP-A-6-61314, patterns of an indeterminate form are registered because known patterns to be used for comparison are produced on the basis of actual wafers. The method in the U.S. Pat. No. 5,982,920 makes clusters of various forms of lines or of indeterminate forms be classified mixed as one type. In either case, when the cause of defect is specified by manpower, skill is required. For automatic inspection, an enormous amount of data must be accumulated, and as a result the computation time increases. Therefore, information that makes the defect cause identification by manpower easy is required to be fast produced.

In order to achieve the above object, according to the invention, there is provided a defect data analyzing method for classifying defects, on the basis of the position coordinates of defects detected by an inspection apparatus, into at least one kind of distribution feature category, or any one of repetitive defect, congestion defect, linear distribution defect, ring/lump distribution defect and random defect.

According to the invention, since a high-density region image representing a high-density portion of defects is generated on the basis of the position coordinates of defects detected by an inspection apparatus, the high-density region is not required to recognize as cluster, and a relatively high-density region can be extracted even if the distribution is thin. Moreover, according to the invention, since the high-density region image is classified into any one of a plurality of previously registered geometric patterns, the defect distribution states can be analyzed at a practical level in both computing time and storage capacity. Since meaning can be previously created in each of the plurality of geometric patterns, the cause of defect in apparatus or process can be identified with ease.

Other objects, features and advantages of the invention will become apparent from the following description of the embodiments of the invention taken in conjunction with the accompanying drawings.

BRIEF DESCRIPTION OF THE DRAWINGS

FIGS. 6A–6F are diagram useful for explaining a method of identifying linear distribution defects.

DESCRIPTION OF THE EMBODIMENTS

Embodiments of the invention will be described with reference to the accompanying drawings.

Figure 1:
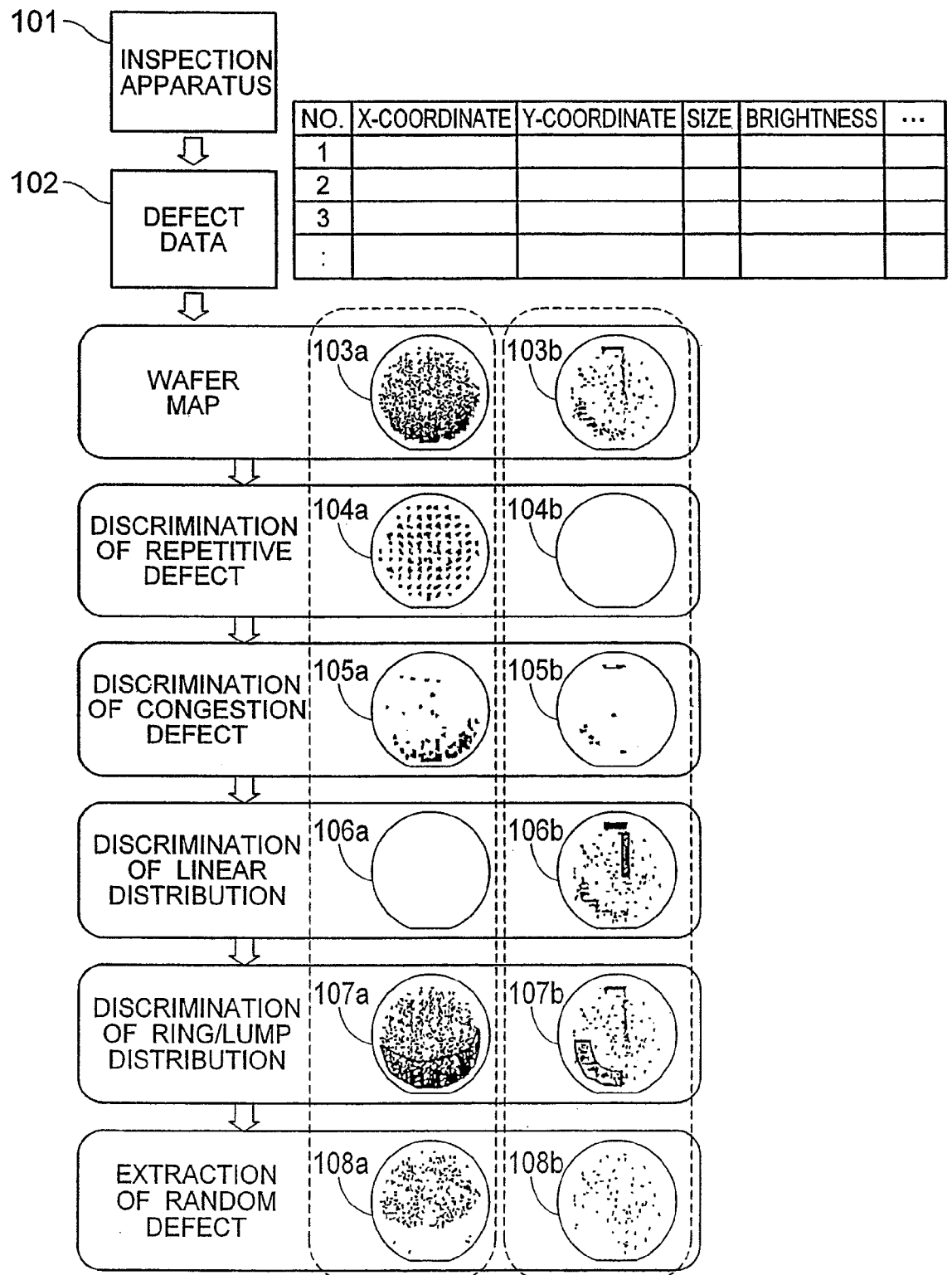
FIG. 1 is a process flow diagram showing the idea of the defect data analyzing method according to the invention.

FIG. 1 is a diagram showing the idea of the defect data analyzing method according to the invention.

In the first embodiment of the defect data analyzing method according to the invention, defect data 102 produced from a semiconductor substrate inspection apparatus 101 includes at least the coordinates of defect position. Shown at 103a, 103b are wafer maps for showing the positions of defects expressed by a coordinate system with its origin selected as one point from the wafer. The coordinates of defect that the inspection apparatus produces can be expressed by a coordinate system with its origin selected as one point from the wafer or by coordinate systems with their origins selected from the respective chips of the wafer. In the former case, the coordinate values X, Y of defect are used as they are, but in the latter case it is necessary that the coordinates of defect within a chip be converted to be on another coordinate system by using chip arrangement information and chip size information. The defects on the wafer map are respectively classified on the basis of its defect distribution into distribution characteristic categories by the discrimination processing of repetitive defect, congestive defect, linear distribution, ring/lump-shaped distribution and extraction processing of random defect.

Figure 2:
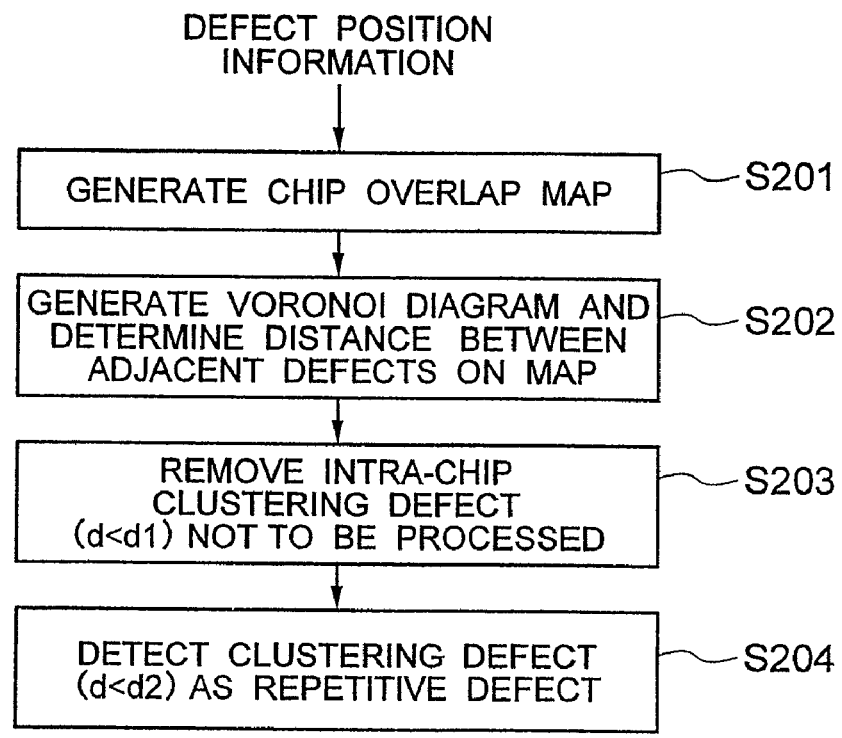
FIG. 2 is a flowchart showing the procedure of repetitive defect identification processing.
Figure 3:
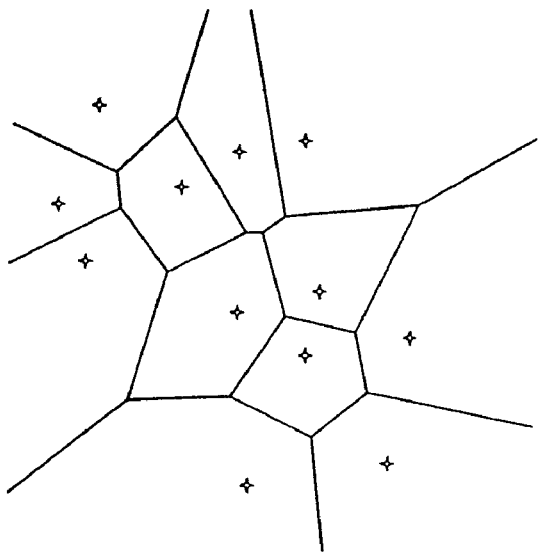
FIG. 3 shows an example of a closest point Voronoi diagram.

The repetitive defect occurs over a plurality of chips to be at substantially the same positions within each chip. Shown at 104a, 104b is the repetitive defect as indicated by dots corresponding to those in the maps 103a, 103b. FIG. 2 is a flowchart for the repetitive defect discrimination. First, a chip overlap map is generated from the defect position coordinates so that all defect positions can be expressed by the coordinates based on the respective origins of chips (S201). When the coordinates of defect positions are expressed by the coordinate system covering all the wafer, it is necessary to convert them by use of chip arrangement and chip size information so that they can be shown on the coordinate systems having their origins on the respective chips. Then, a closest point Voronoi diagram is produced to determine the distances between the adjacent defects on the chip overlap map (S202). FIG. 3 shows an example of the closest point Voronoi diagram. The closest point Voronoi diagram represents the area of influence of each coordinate point. The area of influence of coordinate point P is defined as a set of closest points of P. The influential area is expressed by a polygon surrounding the point P, and called Voronoi region of P. The corresponding points of other regions coming contact with the Voronoi region of P are the points adjacent to P. Defects having a cluster within a chip, or having adjacent defects within the same chip with the distance d between them equal or less than a predetermined threshold d1 are excluded not to be processed (S203). The remaining defects forming a cluster, i.e., defects with the distance d equal to or less than a predetermined threshold d2 are combined to be a group, and the group having defects of which the number is equal to or less than a specified value is detected as repetitive defect (S204). The repetitive defect has its group number attached for each group. The coordinates within chip, the constituent defect number, chip number that characterize the group are calculated and recorded.

The congestion defect has a very small distance to the adjacent defect on the wafer map, and normally called cluster defect. Shown at 105a, 105b are congestion defects that correspond to those of the maps 103a, 103b as indicated by dots. For congestion defect discrimination, defects with the distance equal to or less than a predetermined threshold are connected to form a group, and the group having a predetermined number of defects is detected as congestion defect. A closest point Voronoi diagram corresponding to the wafer map is generated to determine the distances between the adjacent defects, and it is checked if the distance to the adjacent defects is equal to or less than a threshold. Alternatively, the wafer map is partitioned into lattice areas, and it is previously examined which lattice each point belongs to. It is possible to check if the distance between the defects in the same lattice or in the adjacent lattices is equal to or less than a threshold. The congestion defect has its group number attached for each group, and the gravitation center coordinates, maximum x/y coordinates, minimum x/y coordinates, area, defect density and constituent defect number that characterize the group are calculated and recorded.

The linear distribution defect has a linear distribution of high-density defects. The portion surrounded by a square in 106a, 106b shows the linear distribution defect corresponding to that of 103a, 103b. The linear distribution does not strictly show a straight line, but has a certain width.

The ring/lump distribution is a distribution having a ring-shaped or lump-shaped distribution of high-density defects. The portions surrounded by the solid line in 107a, 107b show the ring/lump distribution defect corresponding to those in 103a, 103b.

The other type of detect than the above types of defect is extracted as random defect. Shown at 108a, 108b are the random defects that correspond to those in 103a, 103b.

The linear distribution defect identifying method according to the invention will be described in detail with reference to FIGS. 4A~6.

Figure 4A:
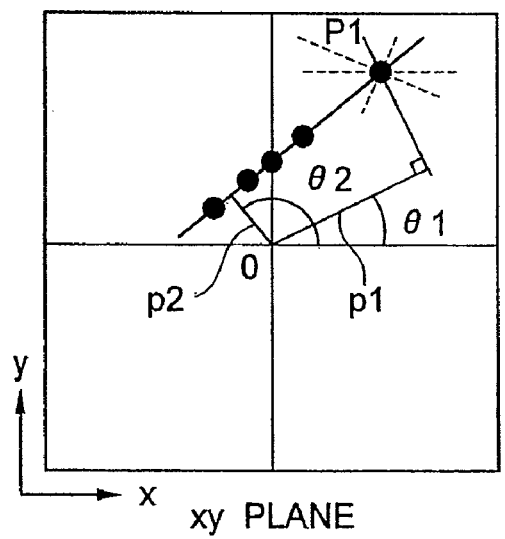
FIGS. 4A and 4B are graphs useful for explaining the principle of Hough transform.
Figure 4B:
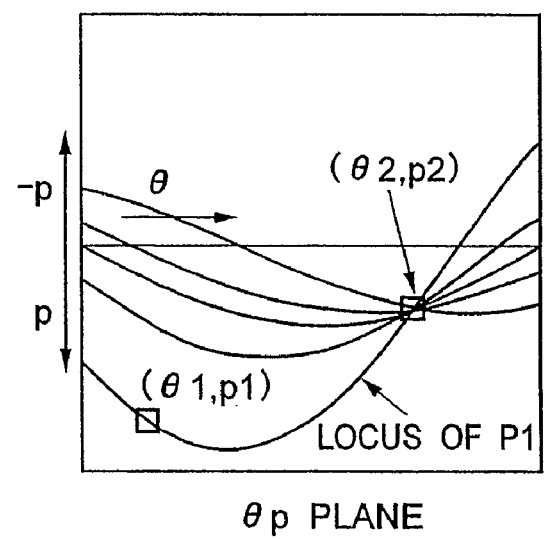

Hough transform is often used for linear detection. FIGS. 4A, 4B are diagrams useful for explaining the principle of Hough transform. As illustrated in FIG. 4A, a straight line on the x-y plane can be expressed by two parameters of the distance $\rho$ from the origin and angle $\theta$ of the perpendicular to the straight line. When a straight line passing through a point P1 on the x-y plane in FIG. 4A is plotted on a $\theta\rho$ plane in FIG. 4B, the locus becomes a curve passing through points $(\theta_1, \rho_1)$, $(\theta_2, \rho_2)$ as shown in FIG. 4B. For other points on the x-y plane, curves can be depicted similarly. When a group of points is distributed as a straight line as in FIG. 4A, the loci of straight lines passing through each point become curves intersecting at the point $(\theta_2, \rho_2)$ as shown in FIG. 4B. Therefore, the groups of points on the x-y plane are converted to the loci on the $\theta\rho$ plane, and of the points $(\theta,\rho)$ at which those loci, or curves intersect, a maximal point $(\theta,\rho)$ at which a maximum number of curves intersect is determined so that a straight line corresponding to the maximal point $(\theta,\rho)$ can be detected.

Figure 5:
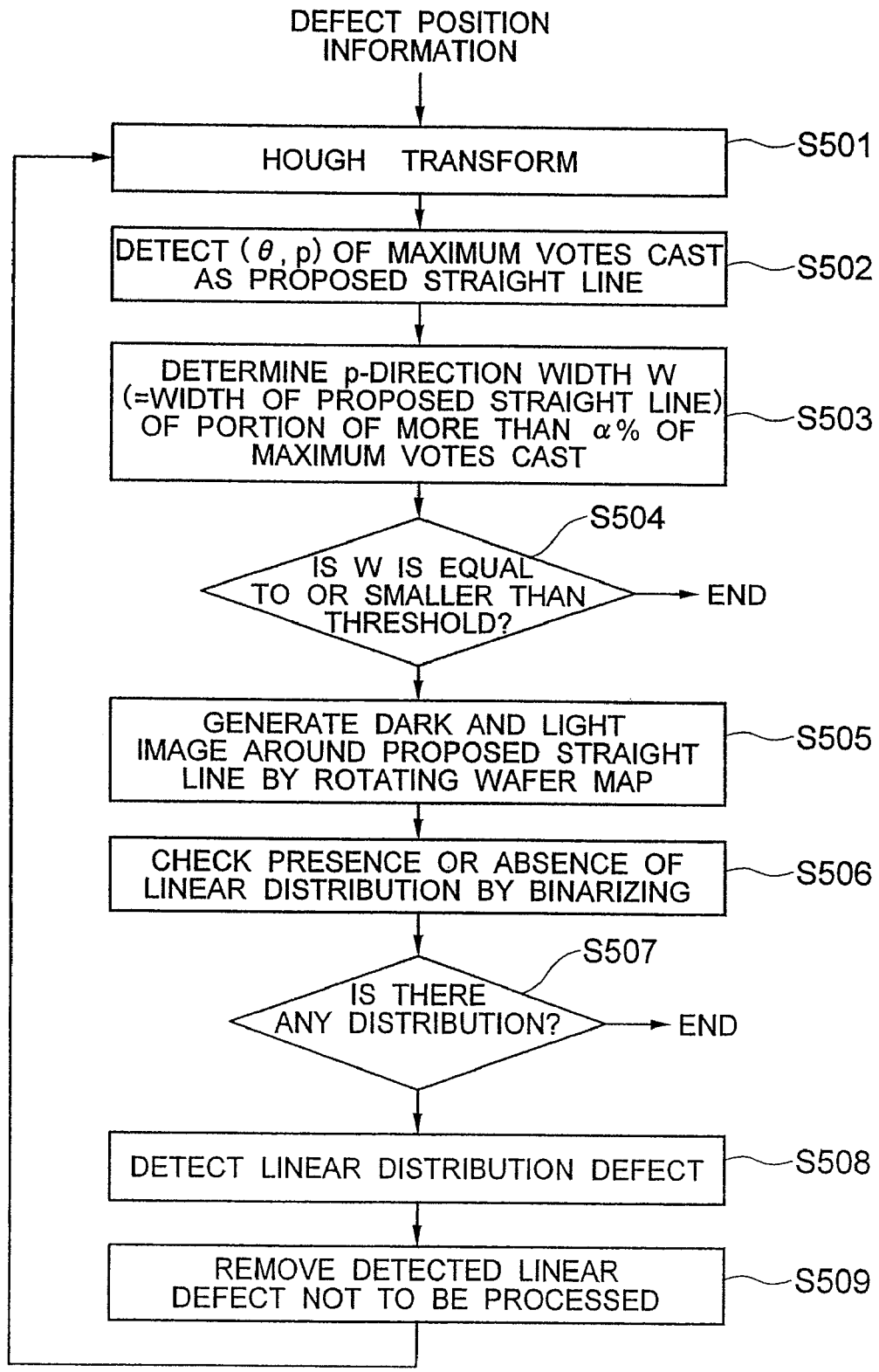
FIG. 5 is a flowchart of the procedure of identifying linear distribution defects.

Hough transform is also used for the identification of linear distribution defect according to the invention. FIG. 5 is a flowchart of the linear distribution defect discrimination. FIGS. 6A~6F show an example of the processing. First, Hough transform is made for defect coordinates (S501), and a straight line corresponding to the point of coordinates ($\theta$, $\rho$) at which the maximum number of the curves intersect, or the number of ballots cast is the maximum, is detected as a proposed straight line (S502). FIG. 6B shows an image, after Hough transform, of wafer map of FIG. 6A. Since the linear distribution has a certain width as described above, the resolution of ($\theta$, $\rho$) is made rough. When normal Hough transform is performed, however, a problem occurs that, if congestion defect is located in two places, a straight line connecting the two congestion defects is detected. Since the congestion defect can be considered as being linearly distributed, removal of congestion defect also could adversely affect the results. To solve this problem, weighting proportional to the distance between the defects or the square of the distance between the defects is performed at the time of casting ballots to ($\theta$, $\rho$), thus reducing the contribution of the congestion defects. To this end, it is necessary to previously generate a closest point Voronoi diagram for wafer map and calculate the distances between the defects. If the Voronoi diagram is already generated at the time of congestion defect discrimination, it may be used. In addition, since there is only one defect within the Voronoi region, the reciprocal of the area of the Voronoi region can be considered as the local defect density at the corresponding coordinates. The reciprocal of the defect density, i.e., the Voronoi region area may be used for the above weighting.

Then, the width W in $\rho$-direction is determined of the portions of $\alpha$ % of the maximum ballot number of the proposed straight line as shown in FIG. 6B (S503). The value $\alpha$ is a predetermined threshold, and W can be considered as the width of the proposed straight line. Next, it is checked if W is equal to or less than the predetermined threshold. If it is larger than the threshold, i.e., if the width is too wide, it is decided that there is no linear distribution, and the processing ends (S504). If it is smaller than the threshold, the wafer map is rotated by $-\theta$, and a dark and light image is generated that shows the density of the periphery of the proposed straight line (S505). At this time, the pixel size is made equal to W. The lattices shown in FIG. 6C are associated with the pixels of the dark and light image. In the figure, however, the lattices are shown rotated $\theta$ in place of rotating the wafer map by $-\theta$. The dark and light image is generated so that large pixel values are given for lattices of high-density defects and that the small pixel values are given for the lattices of low-density defects. For example, the pixel value is determined in proportion to the number of defects within lattice. The same weighting may be made as at the time of Hough transform processing for reducing the contribution of the congestion defect.

Then, a proper method such as discrimination analysis method is used to binarize the dark and light image as shown in FIG. 6D, and the presence or absence of any linear distribution is decided from the binary image (S506). The black sections in FIG. 6D can be considered as candidates of linear distribution defect. Since the center line is associated with the position of the proposed line, the decision of the presence or absence of any linear distribution is performed by digitalizing the length of a proposed line of defects at the center, the continuity or not, the presence or absence of side distribution lines, and comparing them with specified thresholds. In the example of FIG. 6D, the square portion surrounded by the solid line in FIG. 6E can be decided to be a linear distribution. If there is no linear distribution, the processing ends (S507). If there is any linear distribution, the portion of FIG. 6E is rotated by $\theta$ to be aligned with the corresponding portion on the wafer map as shown in FIG. 6F, and the defects within the solid-line square are detected as a linear distribution defect (S508). The detected linear distribution defect is removed not to be processed next (S509), and the steps from S501 are repeated. Each linear distribution detected during one cycle of the processing is attached with a group number, and the amounts of characteristics such as position, width, angle, length and defect density are calculated and recorded.

Figure 7:
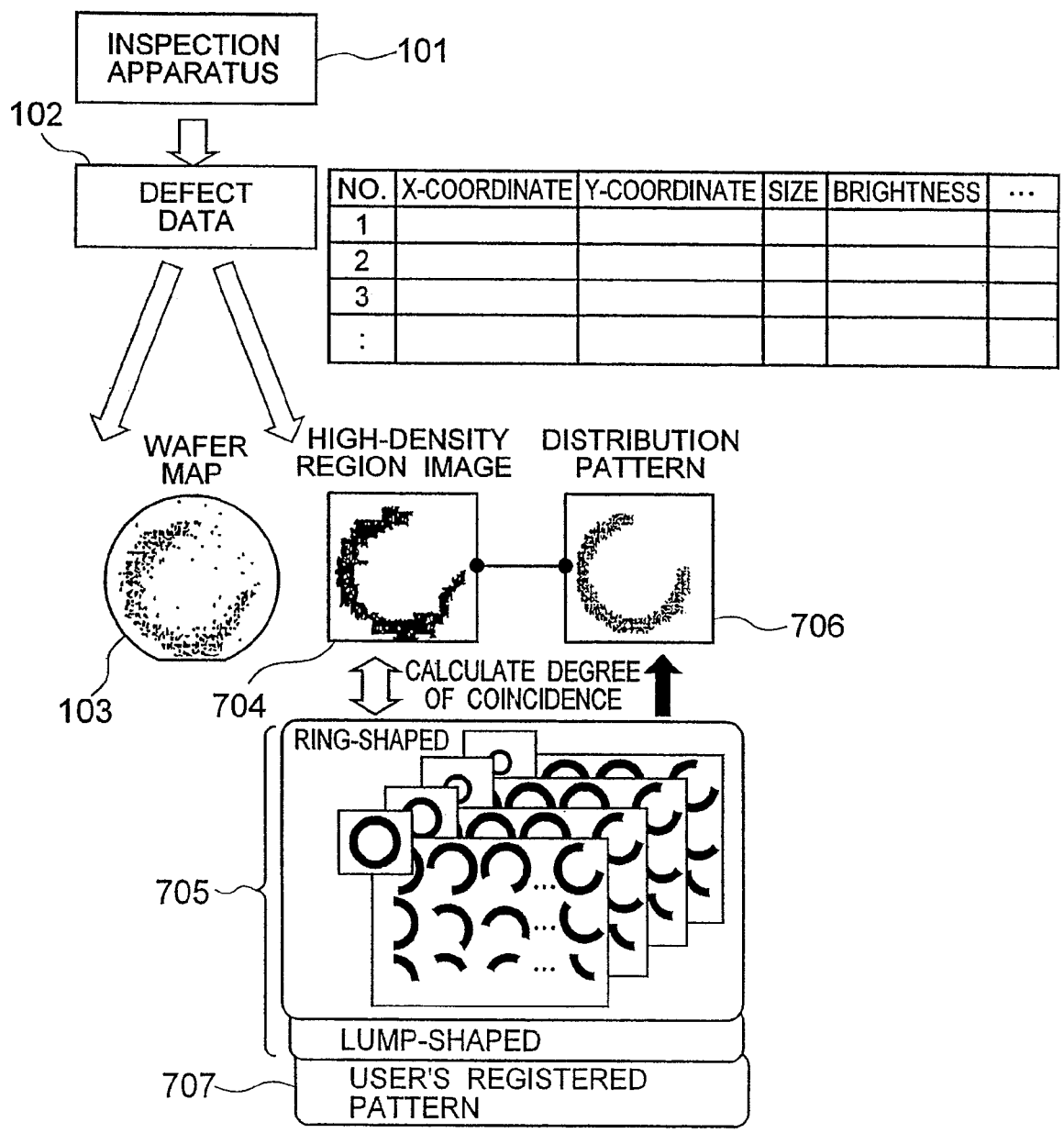
FIG. 7 is a diagram showing the idea of identifying ring/lump distribution defects.

The ring/lump distribution defect identifying method of the invention will be described in detail. FIG. 7 is a diagram showing the concept of the ring/lump distribution defect identifying method of the invention. In the first step, a binary image having 1's indicating high defect density and 0's indicating low defect density is generated on the basis of the coordinates of defects. This image will be hereafter called a high-density region image 704. In the next step, a plurality of geometrical dictionary pattern images 705 are automatically generated according to the size of the high density region image 704. Next, the degree of coincidence between the high density region image 704 and each of the plurality of geometrical dictionary pattern images 705 is calculated, and in the last step, a pattern image 706 of the highest degree of coincidence is selected. According to another aspect of the invention, dictionary patterns 707 are previously registered by the user except the automatically generated geometrical dictionary pattern images 705, and the pattern image 706 of the highest degree of coincidence is selected from those patterns 705, 707. The pattern image 706 and wafer map 103 are overlapped, and the defects included within the pattern portion are detected as a ring/lump distribution defect.

Each step will be described in detail.

A description will be first made of a method for producing the high density region image 704 on the basis of the defect position coordinates.

Figure 8:
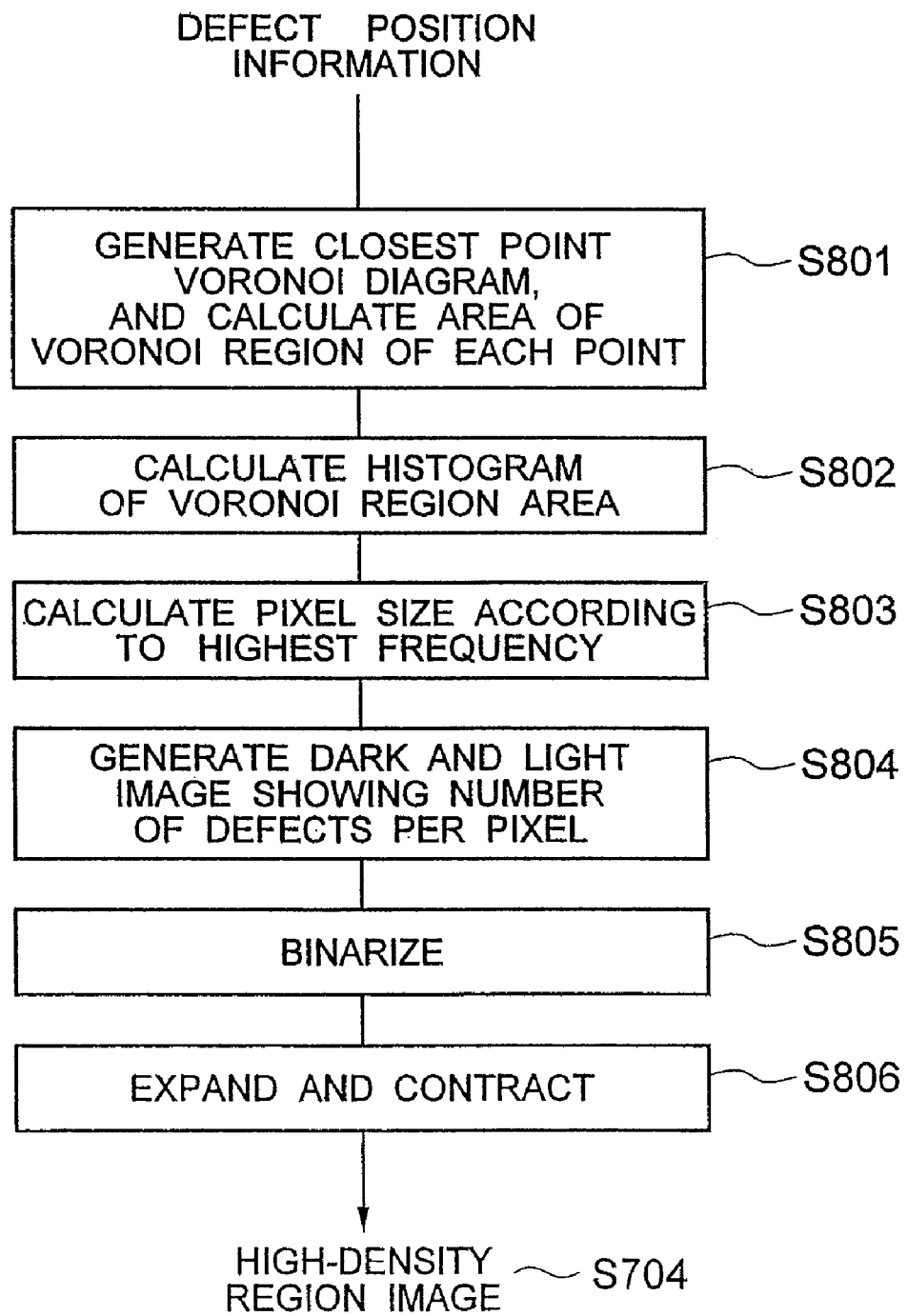
FIG. 8 is a flowchart of the procedure for making a high-density region image.

FIG. 8 is a flowchart for the generation of high density region image 704.

First, a closest point Voronoi diagram for all defect coordinates is generated, and the area of the Voronoi region at each point is determined (S801). If this calculation is made in the above linear distribution defect discrimination processing, the calculation result may be used. Then, the histogram of the area of the Voronoi region is calculated (S802). In this case, the defects classified as any type of repetitive defect, congestion defect and linear distribution defect are not included in the calculation of histogram. The highest frequency value is determined from the histogram, and multiplied by a predetermined number (assumed as N), and the square root of the multiplication result is calculated and used as the image size (S803). The image size is determined so that the whole wafer can be fallen just within a single image, and a dark and light image is generated with the number of defects per pixel being expressed by tint (S804). This image is generated by incrementing the pixel value at the coordinates of each defect with all pixels initially set to 0. At this time, when N is too large, the image size becomes small, making it difficult to discriminate shapes, and thus N should be selected to be about 5. If N is too small contrary to the above case, the thickness difference between the high-density and low-density portions becomes small, making it difficult to discriminate. Next, the image is binarized by use of a predetermined threshold (represented by T) to be a binary image of 1's indicating high density portion and 0's indicating low density portion (S805). Here, T and N should be made substantially equal. The obtained image has a pattern of a relatively high defect density. Finally this pattern undergoes expansion and contraction processing to form the high-density region image 704 (S806). Thus, by generating the image using this method, a relatively high density region can be extracted with a proper image size set even if the image has a thin distribution. In addition, another method can be considered in which the dark and light image is generated in step S804 and binarized in step S805. Each defect is weighted in proportion to the shortest distance to the adjacent defect, the square of the shortest distance or the Voronoi region area, and added to the pixels at the corresponding positions, thereby generating the dark and light image. This image is binarized by use of a discrimination analysis method.

A description will be made of the method for automatically producing the geometric dictionary pattern images 705.

The geometric dictionary pattern images 705 are automatically generated with the ring pattern and lump pattern separated. The image size is determined as with that of high-density region image 704. The pattern is generated by using the largest circle to be depicted on the image as a reference according to the following method.

Figure 9:
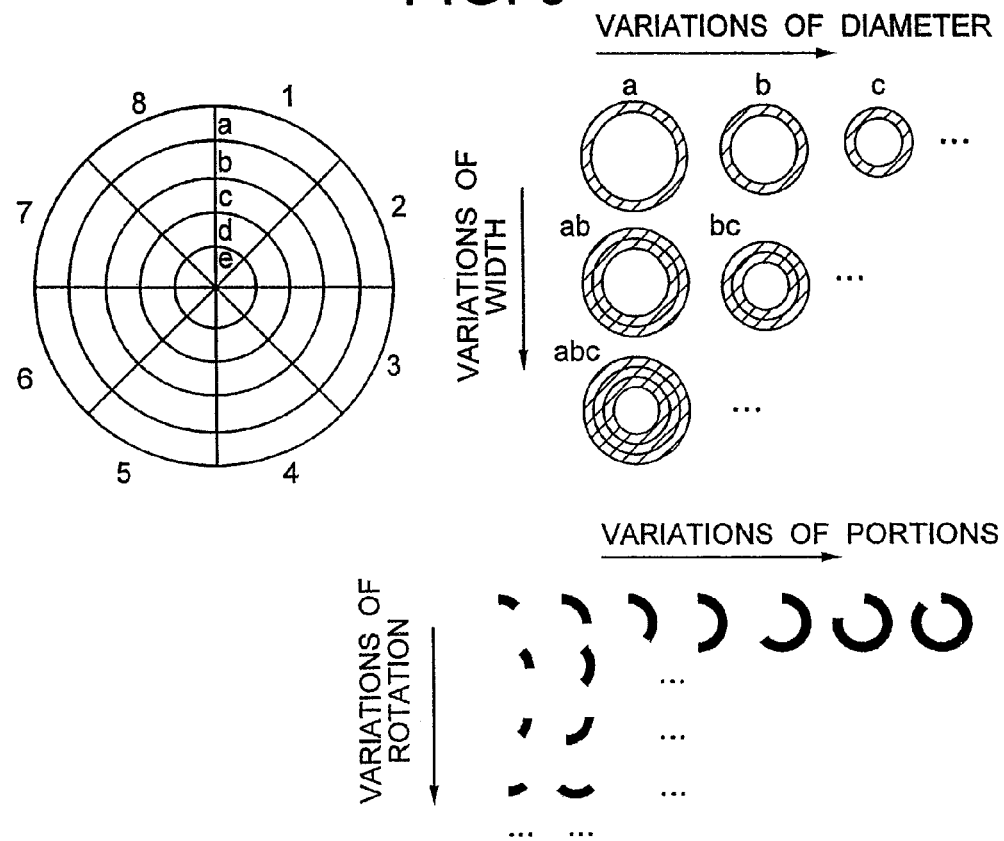
FIG. 9 is a diagram to which reference is made in explaining a method of automatically producing ring-shaped dictionary patterns.

The ring patterns are generated by dividing the reference circle equally in the radius direction to be concentric circles, and combining small regions resulting from equal fan-shape division of the circles toward the central angle as shown in FIG. 9. A method of combining the small regions will be described with reference to FIG. 9 that shows the patterns resulting from five division in the radius direction and eight divisions in the central angle direction. The circular rings (of which the innermost one is a circle) resulting from the division in the radius direction are attached with symbols of a, b, c, d, and e from the outside, and the eight fan-shaped regions resulting from the division in the central angle direction are numbered 1~8 in turn. The sizes of complete circular rings or circle are combined as 15 combinations of a, b, c, d, e, ab, bc, cd, de, abc, bcd, cde, abcd, bcde, abcde. The segments of the circular rings, have seven different sizes, or variations of an eighth, two eighths, three eighths, four eighths, five eighths, six eighths and seven eighths. The segments of each equal size can be combined as 8 combinations. For example, the segments of two eighths can have 8 combinations of 12, 23, 34, 45, 56, 67, 78 and 81. The total combinations resulting from these combinations plus one circular ring, or 57 combinations can be considered. In addition, since the above-mentioned 15 combinations can be considered for each one of those combinations, a total of 855 patterns can be generated.

The circular rings are not always required to divide as in the radius direction and central angle direction. Also, they are not necessary to divide equally. However, equal division is desirable not to prevent the processing from being complicated.

Figure 10A:
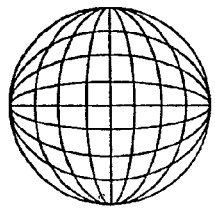
FIGS. 10A–10G are diagrams to which reference is made in explaining a method of automatically producing lump-shaped dictionary patterns.
Figure 10B:
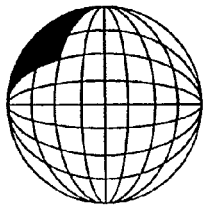
Figure 10C:
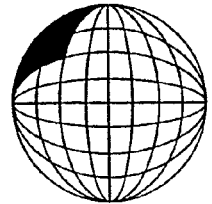
Figure 10D:
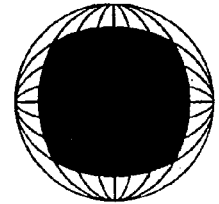
Figure 10E:
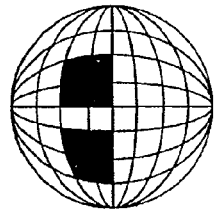
Figure 10F:
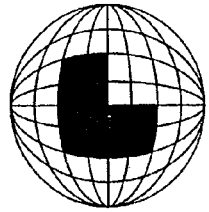
Figure 10G:
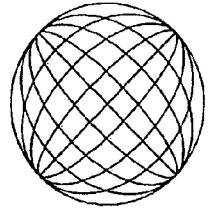

The lump-shaped patterns are generated by dividing the reference circle equally in the horizontal direction by elliptical shapes with the long axis selected as the vertical diameter, dividing equally in the vertical direction by elliptical shapes with the long axis selected as the horizontal diameter and combining the resulting small regions. FIG. 10A shows 8 divisions of the circle in each direction of the horizontal and vertical directions. The total number of combinations of horizontal sizes and positions is 36 since 8 sizes from 1 to 8 and (9-N) positions when the size is N can be considered. The total number of combinations of vertical sizes and positions is the same. Therefore, since the horizontal and vertical sizes and positions can be freely combined, 1296 different patterns can be generated. FIGS. 10B~10D show examples of these patterns generated in this way as indicated by the black areas. The combinations of separate regions and a pattern having a recess as shown in FIG. 10F cannot be generated in this way. It can also be considered that a pattern generated in the above way is rotated 45 degrees around the center of the reference circle to be another lump-shaped pattern. FIG. 10G shows the small regions formed by division in this case. Either case or both cases may be used. The number of divisions may be other than 8.

By automatically generating the geometrical dictionary pattern images 705 in the above way it is possible to suppress the pattern number to a practical level, and thus achieve fast processing.

Figure 11:
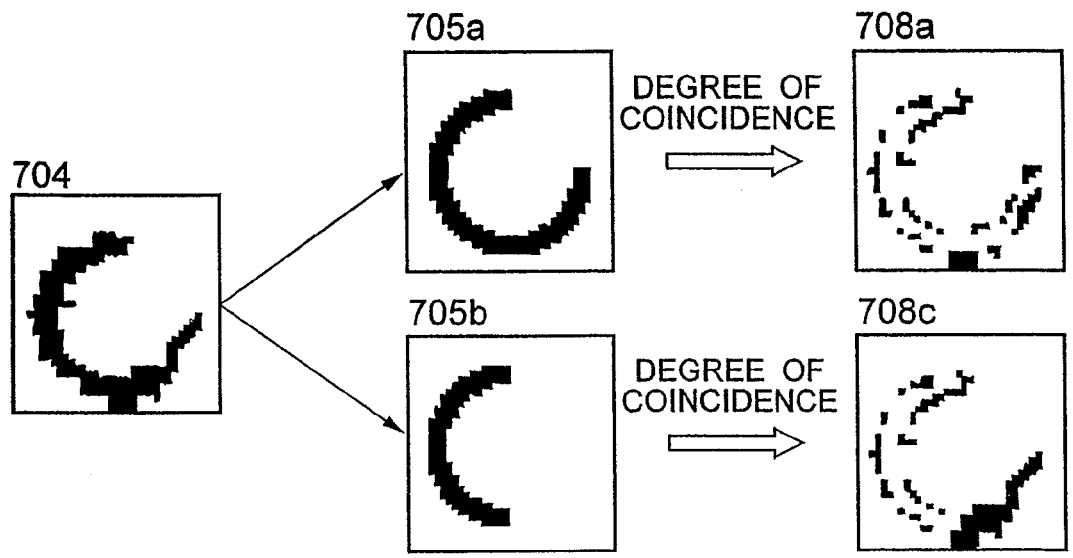
FIG. 11 is a diagram useful for explaining a method of computing the degree of coincidence between the high-density region image and each of the dictionary pattern images.

A description will be made of a method for calculating the degree of coincidence between the high-density region image 704 and each of dictionary pattern images 705 with reference to FIG. 11. Each pixel value of high-density region image 704 is compared with that of dictionary pattern image 705 at the same address. If coincidence is reached, +1 is produced. If coincidence is not reached, −1 is produced. All the pixels are compared similarly. The results of the comparison of all pixels are added up, and the total is regarded as the degree of coincidence. FIG. 11 shows the high-density region image 704 and parts 705a, 705b of the dictionary pattern image with the pixel value 1 indicated by black and 0 by white. Also 708a and 708b represent mismatched portions of the high-density region image 704 with the dictionary pattern image 705a, 705b as indicated by black. In other words, the pixel values of the white portions of these images are 1, those of the black portions are −1, and the total of all pixel values is the degree of coincidence. When compared with image 708b, the image 708a is found to have a smaller black area, and thus the degree of coincidence of the pattern 705a with the high-density region image 704 is higher than the pattern 705b.

In the above method, the pattern 706 is detected without fail, but in practice, it should be decided that any pattern is not produced at all when the density is very low or when the density difference is small. Therefore, the detected pattern 706 is verified so that the presence and absence of pattern is decided. A description will be made of a method for deciding the presence or absence of pattern and a method for adjusting the sensitivity of pattern detection. In order to decide the presence or absence of pattern, it is necessary that a dark and light image be generated by a weighting method and used when the high-density region image 704 is produced. The detected pattern image 706 and the dark and light image are superimposed on each other, and the ratio C of decision analysis values of the inside and outside of pattern is calculated from the pixel values of the dark and light image according to the following equation.

$$C = \frac{\omega_p \omega_b (\mu_p - \mu_b)^2}{\omega_p \sigma_p^2 + \omega_b \sigma_b^2} \quad (1)$$

$\begin{cases} \omega_p, \omega_b : \text{numbers of pixels in and out of pattern} \\ \mu_p, \mu_b : \text{average values of pixel values of dark and} \\ \quad\quad\text{light image in and out of pattern} \\ \sigma_p, \sigma_b : \text{standard deviations of pixel values of dark and} \\ \quad\quad\text{light image in and out of pattern} \end{cases}$ The ratio C is compared with a predetermined threshold. If it is equal to or smaller than the threshold, it is decided that there is no pattern. In addition, if the highest frequency is lower than a predetermined value in the histogram obtained in step S802, it is decided that there is no pattern without making the following processing. If the former threshold is selected to be small, a pattern with a smaller density difference can be detected. If the latter threshold is set to be small, a pattern with a smaller defect density can be detected. Therefore, if these thresholds are specified by the user, the user can adjust the sensitivity.

Figure 12:
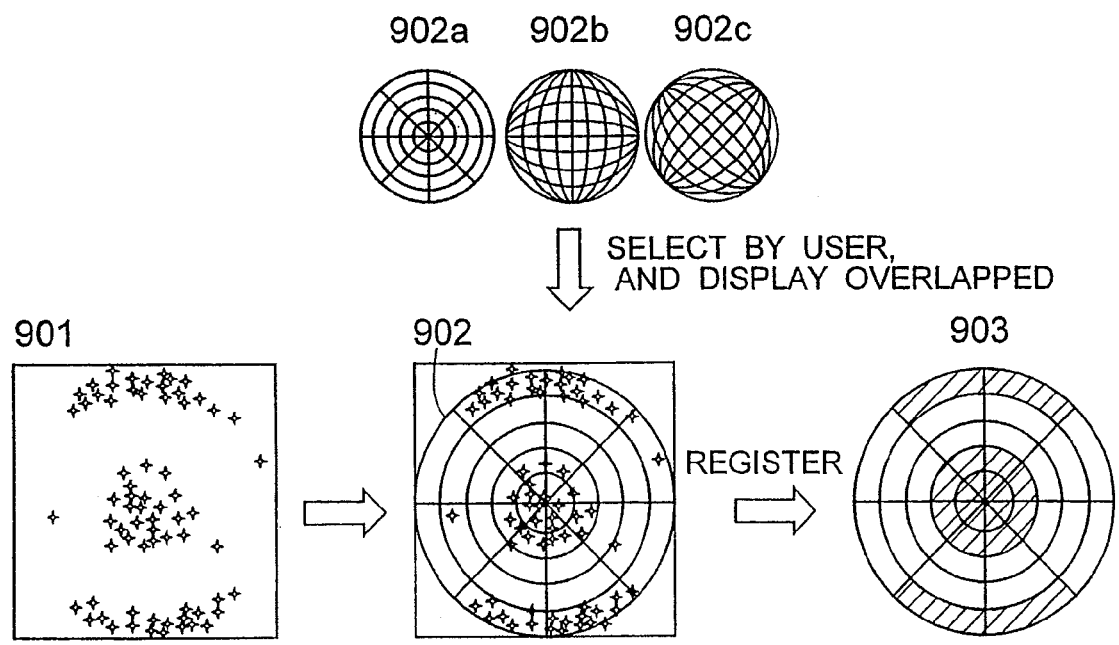
FIG. 12 is a diagram useful for explaining a method of computing the degree of coincidence between the high-density region image and each of the dictionary pattern images.

Incidentally, the semiconductor substrate is not always examined for all surface because of the restriction to the throughput, but it is often partially examined by specifying inspection or no inspection for each row of chips. In this case, it is difficult for the pattern detection to be made by the above ring/lump discrimination method. Another method for discriminating ring/lump distributions with the above problem solved will be described with reference to FIG. 12. FIG. 12 is a diagram showing the idea of ring/lump distribution discrimination that can be used for the defect data on the wafer to be partially examined. When partial examination is executed, the wafer map 103 is, for example, as illustrated. The high-density region image 704 is generated, and geometric dictionary pattern 705 is automatically produced, by the same method as above. On the other hand, a region image 709 to be inspected is generated on the basis of inspection condition information and chip matrix data. The region image 709 to be inspected and each geometric dictionary pattern 705 are superimposed, and the degree of coincidence is calculated with the non-inspection region used as a mask. In other words, the dictionary pattern image 705 and region image 709 to be inspected of high-density region image 704 are simultaneously scanned, and the following operations are made. The pixel value is 0 for the non-inspection region. In the case of inspected region, if the pixel values of high-density region image 704 and dictionary pattern image 705 are matched, +1 is given, and if they are not matched, −1 is given. Those values are added up over all pixels, and the total is regarded as the degree of coincidence. In this way, the degree of coincidence is calculated to each dictionary pattern image 705, and the pattern image 706 with the highest degree of coincidence is selected. According to this method, the degree of coincidence to dictionary pattern 705 can be calculated with high precision even in the case of partial inspection, thus making it possible to discriminate ring/lump distribution defects.

The user pattern registration method will be described below.

Figure 13:
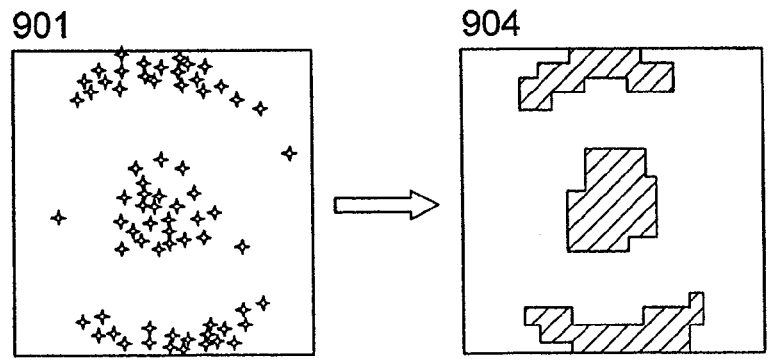
FIG. 13 is a diagram showing a first method for user pattern registration.

FIG. 13 is a diagram useful for explaining the user pattern registration method. First, the user designates a wafer map 901 that has patterns to be wanted to register, and allows it to be displayed on the screen. This designation may be omitted, and in this case nothing is displayed. Then, one pattern is selected from divided patterns 902a~902c that are used for automatic generation of geometric dictionary patterns. Reference numeral 902a represents the same as the ring-shaped pattern shown in FIG. 9, and 902b and 902c are the same as the lump-shaped patterns shown in FIGS. 10A and 10G, respectively. The selected pattern 902 is displayed overlapped on the wafer map 901. The respective small regions of the selected divided pattern 902 are switched to be selected or not selected by the user's designation, and the selected region is displayed in a different color. The user selects small regions at high-density positions or selects those freely, and after the selection the user orders to register. The combination of specified small regions is compared with the automatically generated pattern. If no one is included in the automatically generated pattern, a pattern image 903 is stored as the user's registrated pattern 707. According to this method, if the combination of selected small regions but not pattern image is encoded and recorded as user's registrated pattern, satisfactory results can be obtained.

Figure 14:
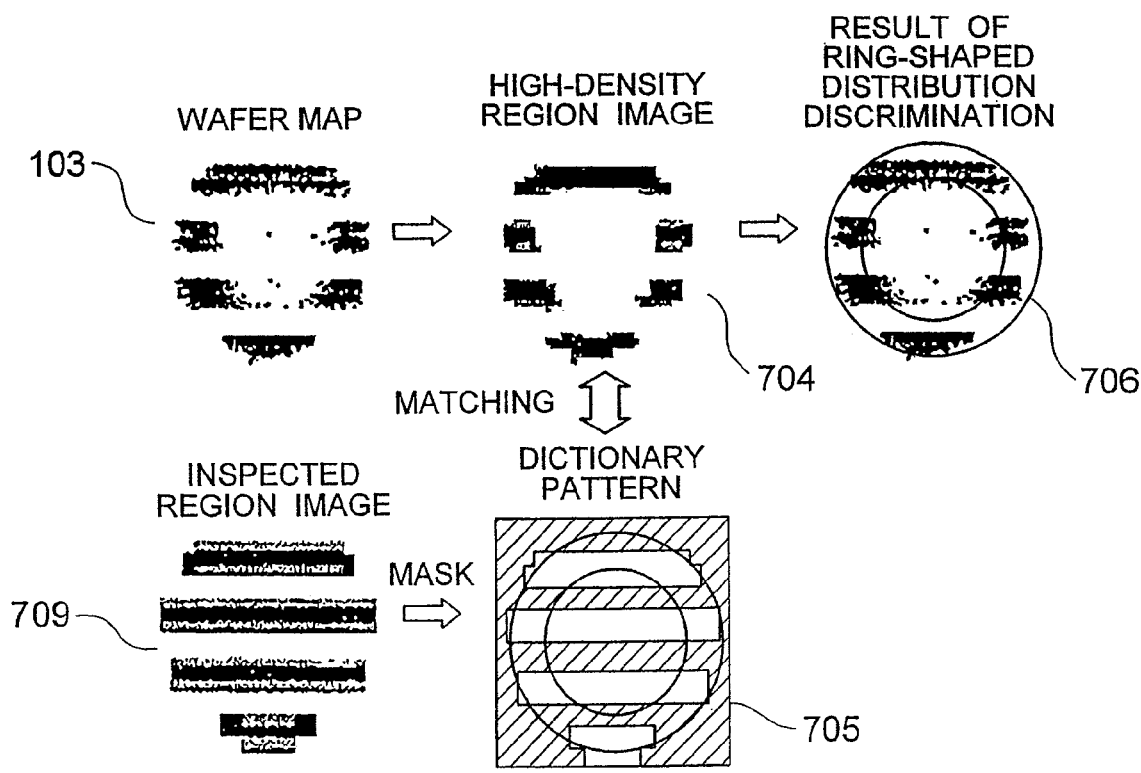
FIG. 14 is a diagram showing a second method for user pattern registration.

FIG. 14 is a diagram to which reference is made in explaining a user pattern registration method different from the above. The user designates the wafer map 901 that has patterns to be wanted to register, and allows it to be displayed on the screen. A high-density region 904 is generated and displayed by the above-mentioned high-density region image generation method. The high-density region 904 is compared with the automatically generated dictionary pattern and the previously registered user's registered pattern so that the degree of coincidence thereto can be calculated. If the maximum degree of coincidence is equal to or smaller than a predetermined threshold, it is registered as user's registered pattern 707. In this case, the user's registered pattern 707 can be recorded as image data.

The user pattern registration method may include both types of method or either one. Also, it may be different from the above one.

In the second embodiment of the defect data analysis method according to the invention, information associated with the automatically generated geometrical dictionary pattern 705 and user's registered pattern 707 is added in the ring/lump distribution defect discrimination processing, and the pattern image 706 is selected according to the same method as in the first embodiment.

The information to be added includes pattern position, size, shape, degree of importance, and specified items. The pattern position, size and shape of the geometrical dictionary pattern 705 are roughly classified according to a constant rule, and default information is added. The positions of the lump-shaped pattern are grouped into upper right, top, upper left, right, center, left, lower right, bottom and lower left. The sizes thereof are classed as large, medium and small, and the shapes are lump. For example, FIG. 10B shows a lump-shaped pattern of small size on the upper left, FIG. 10C a lump-shaped pattern of medium size on the right, and FIG. 10D a lump-shaped pattern of large size at the center. The ring-shaped pattern is selected to be a fourth of a large-radius ring on the upper right. In this case, even if the ring-shaped patter is derived from a lump-shaped patter, it is regarded as a ring-pattern provided that the pattern has only the single outermost row. Even if it is derived from a ring-shaped pattern, it is regarded as a lump-shaped pattern provided that it includes the innermost circle.

Moreover, means is provided for manually grouping the geometrical dictionary pattern 705 and user's registered pattern and collectively adding information, and the same information can be added to the pattern that the user decides to be the same. Accordingly, the resolution of position and size information can be adjusted. The degree-of-importance information is entered by the user. The specific items to be entered include information directly associated with cause of defect.

The first embodiment of the inspection apparatus having the defect data analysis method according to the invention will be described. Hereafter, repetitive defect, congestion defect, linear distribution defect, ring/lump distribution defect and random defect are called distribution feature category. Known inspection apparatus for semiconductor substrate include foreign substance inspection apparatus, optical type pattern defect inspection apparatus and SEM type pattern defect inspection apparatus. The inspection apparatus according to the invention makes inspection for semiconductor substrate by the same known method as either one of these inspection apparatus, classifies the obtained defect data into the distribution feature category by the above method and produces the category information together with the defect data information.

Figure 15:
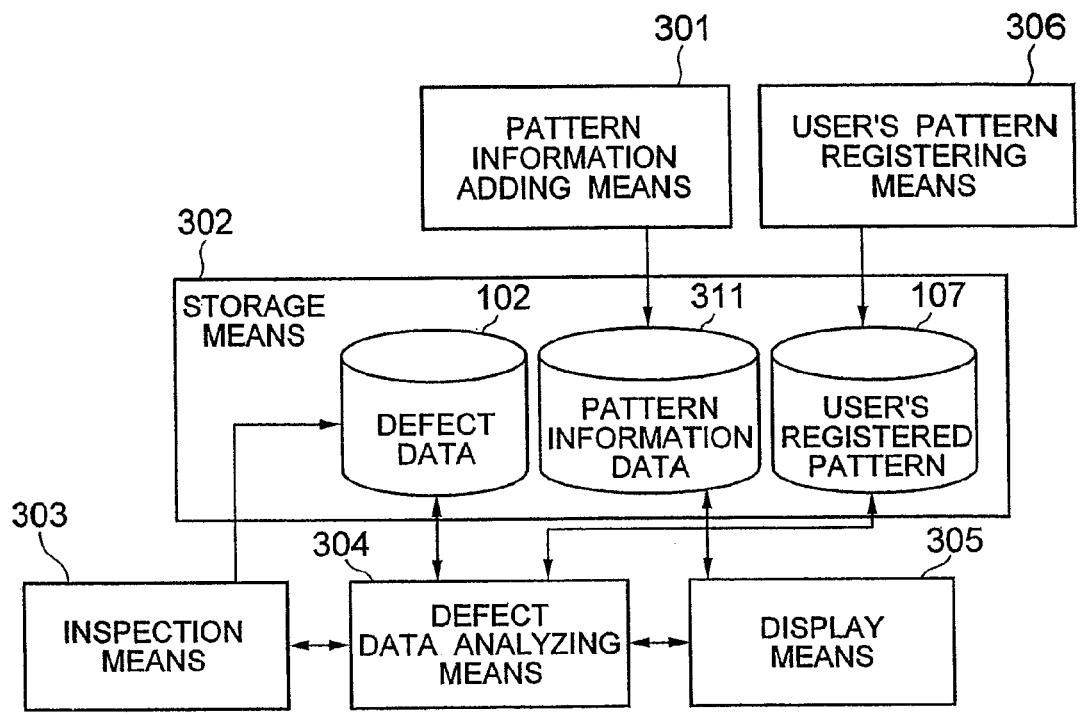
FIG. 15 is a block diagram of a first construction of the inspection apparatus according to the invention.

FIG. 15 is a diagram of the construction of the first embodiment of the inspection apparatus according to the invention.

Pattern information adding means 301 adds pattern-related information such as pattern position, size, shape, degree of importance and specified item to a plurality of automatically generated geometrical dictionary patterns and user's registered dictionary patterns. It has a portion to add default information to the geometrical dictionary pattern, and a portion to manually add information to the geometrical dictionary pattern and user's registered dictionary pattern. The addition of pattern information is made offline. The result is at least once stored as a pattern information file 311 in storage means 302 such as hard disk.

The defect data analysis can be executed in both in-line mode and offline mode.

Inspection means 303 makes wafer inspection by a well known method, and causes defect data 102 including at least defect position coordinates to be stored in the storage means 302.

In in-line mode, the inspection means 303 sends notice of inspection completion to defect data analysis means 304 when inspection of each wafer is finished. The defect data analysis means 304 reads in defect data 102 of each wafer from the storage means 302. Alternatively, it may be so constructed as to transmit and receive defect data 102 without the intervention of storage means 302.

In offline mode, the defect data analysis means 304 is ordered to read in defect data 102 of wafer by the operator.

The defect data analysis means 304 classifies defect data into distribution feature category on the basis of defect position coordinates, and adds distribution feature category number and intra-category group number to defect data of each defect. When a ring/lump distribution defect is detected, it causes the pattern information file 311 to be read from the storage means 302, adds pattern image number or pattern information to the defect data of the ring/lump distribution defect, and makes it be stored in the storage means 302 as defect data 102 including the results of both inspection and analysis. In in-line mode, the inspection means 303 is informed of analysis completion.

The result of classification to distribution feature category is displayed on display means 305. It may be displayed on a wafer map with a different color for each category, or a wafer map may be generated for each category and displayed as shown in FIG. 1. Also, chip overlap maps may be displayed at the same time. In addition, the pattern image 706 selected in the ring/lump distribution discrimination is displayed on the display means 305 together with information associated with the wafer to be inspected and pattern information added to pattern. At the same time, it is stored as an image file in association with the wafer to be inspected. Moreover, when a linear distribution defect is detected, a rectangle that indicates its position is displayed superimposed on the wafer map, and at the same time, information such as position, width, angle, length and defect density is displayed. These information are stored in association with the wafer to be inspected.

User pattern registration means 306 generates user's registered patterns according to the order by the operator, and causes pattern code or pattern image to be stored in the storage means 302, depending on the difference in the above method. It is also possible to construct with the user pattern registration means 306 not provided.

A description will be made of the second embodiment of the inspection apparatus having the defect data analysis method according to the invention. The second embodiment inspects the semiconductor substrate by a well known method, makes the classification to distribution feature category on the basis of the obtained defect data information by the above method, makes sampling on the basis of a specified rule for each category, and produces the classification result and sampling result together with defect data.

Figure 16:
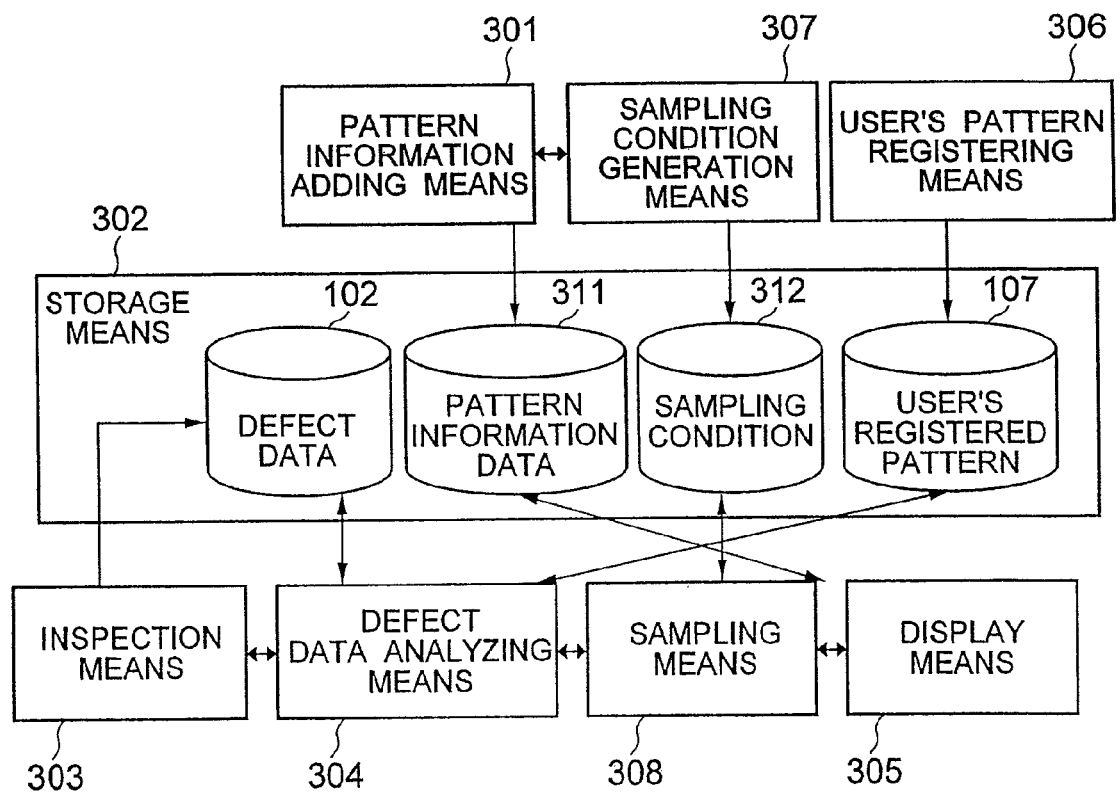
FIG. 16 is a block diagram of a second construction of the inspection apparatus according to the invention.

FIG. 16 shows the construction of the second embodiment of the inspection apparatus according to the invention.

The pattern information adding means 301 adds sampling condition number in addition to the above information. It manually groups the dictionary patterns using the same sampling condition, and attaches the same sampling number. When there is no sampling condition corresponding to the number, sampling condition generation means 307 generates the sampling condition.

The sampling condition generation means 307 generates the sampling condition for determining a defect for review. It manually generates the sampling conditions associated with the patterns of ring/lump distribution defects, and sampling conditions at each of the other distribution feature categories, and makes them be stored as a sampling condition file 312 in the storage means 302. The sampling conditions are, for example, sampling number, sampling rate and sampling method. The values of sampling number and sampling rate are entered after selecting either one for the designation. The sampling number is determined by the sampling rate to the number of defects within a pattern. Sampling manners such as random and defect number order are listed so that the user can select them. When defect number order is specified, sampling is made at intervals matched with the sampling rate.

The operations of the inspection means 303 and defect data analysis means 304 are the same as in the first embodiment.

Sampling means 308, after completion of defect analysis, reads in the sampling condition 312 and the single-wafer defect data 102 with distribution feature information added from the storage means 302. The transmission and reception of defect data 102 may be made without the intervention of the storage means 302. The condition of sampling is determined by the distribution feature category of defect data. If the category is ring/lump distribution defect, sampling is made by use of the condition associated with the added pattern information. If the category is the other one, sampling is made by use of the condition of each distribution feature category. As the result of the sampling, a flag of review or not is added to the defect data, and the defect data 102 including the results of inspection, analysis and sampling is stored in the storage means 302.

Figure 17:
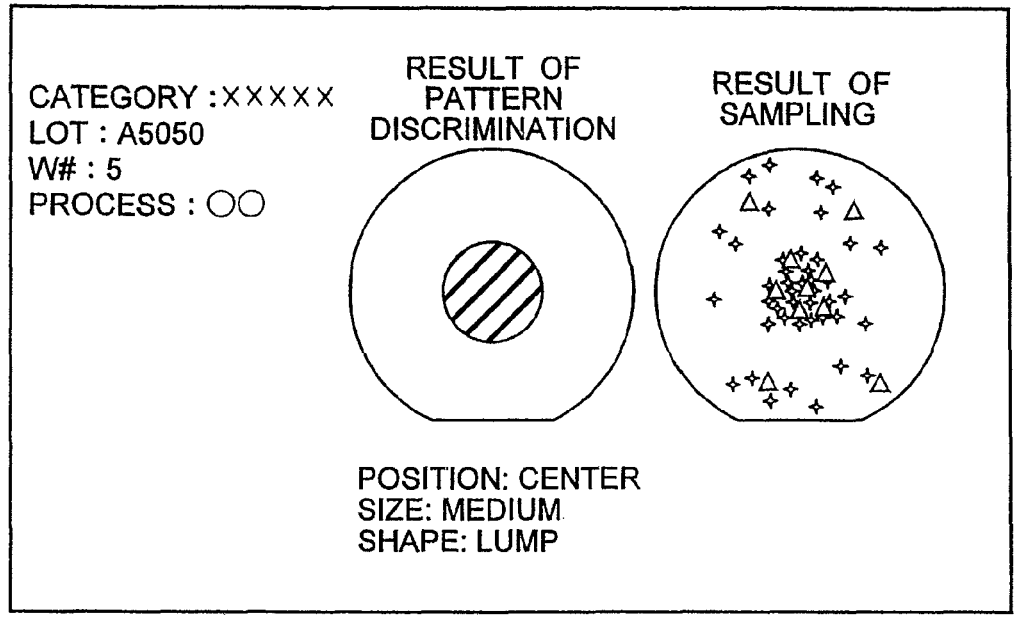
FIG. 17 is a front view of a displayed image showing one example of the image of the defect data analyzed result according to the invention.

The pattern image 706 selected by the defect data analysis means 304 is displayed on the display means 305 together with information associated with the wafer to be inspected, and the pattern information added to pattern. The defect sampled on the wafer map is displayed in a different color or symbol from the other defects. FIG. 17 shows one example of the result image.

The user pattern registration means 306 is operated in the same way as in the first embodiment, but may be omitted.

A description will be made of a review system having the defect data analysis method according to the invention.

Figure 18:
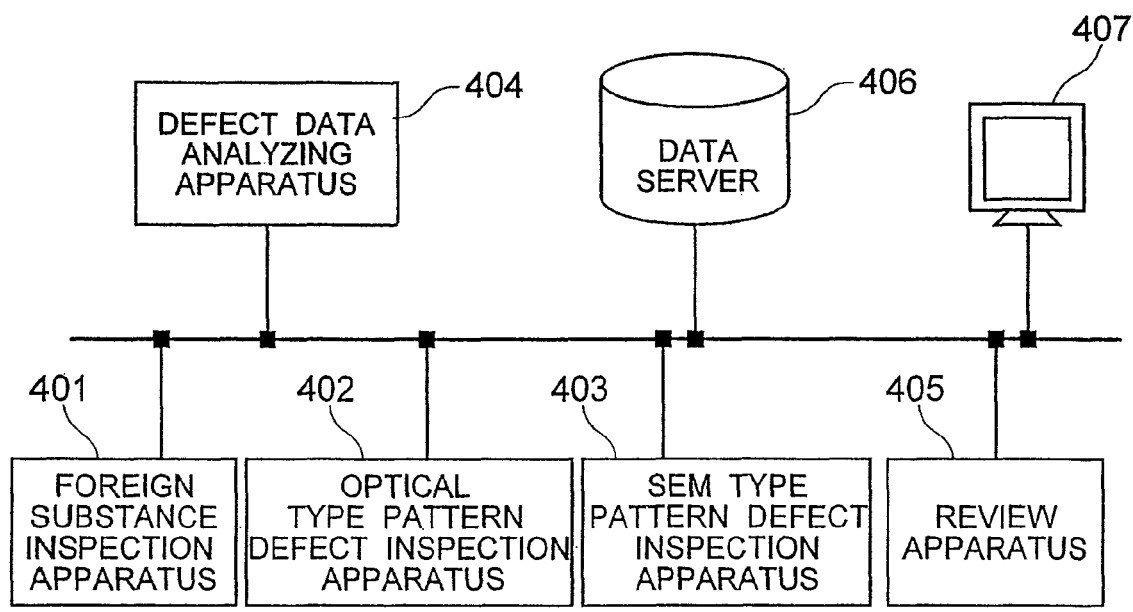
FIG. 18 is a block diagram showing an example of the construction of the review system according to the invention.

FIG. 18 is a diagram of the review system according to the invention.

On a network are connected a foreign substance inspection apparatus 401, an optical type pattern defect inspection apparatus 402, an SEM type pattern defect inspection apparatus 403, a defect data analysis apparatus 404 and a review apparatus 405. Each inspection apparatus 401~403 and the review apparatus 405 are installed within a clean room. The defect data analysis apparatus 404 may be installed anywhere.

The results from the inspection apparatus 401~403 are produced as a file of defect data 102 of the same format, and transferred to the defect data analysis apparatus 404. The defect data analysis apparatus 404 is constructed as in FIG. 12, but has no inspection means 303. It reads in the defect data 102 of the wafer to be analyzed in its defects, and makes classification to distribution feature category and the sampling based on the classification result. The distribution feature information and sampling flag are also added to the defect data 102, produced as a file and transferred to the review apparatus 405.

The review apparatus 405 reads in the defect data 102 with the sampling flag added of the wafer to be reviewed, reviews the defect according to the information and manually or automatically classifies the defect. As a result of classification, a category number is added to the defect data 102, and the defect data is produced as a file and transferred to the defect data analysis apparatus 405. At the same time, the related review image is also transferred. The defect data analysis apparatus 405 generates a report and stores it on the basis of the defect distribution pattern of the wafer to be analyzed, and the defect review result. The content of the report includes information of wafer to be inspected, the result of classification to distribution feature category, and review image. Since distribution feature and defect review image are simultaneously displayed, the cause can be easily presumed. According to user's request, the detailed information such as estimated rate of defect types or other analyzed results by a well known analysis means may be given which are calculated from the sampling position information, review result and sampling rate. Any format may be used for the report, but HTML format is used. The report is uploaded to a data server 406 connected via the Internet or intranet so that it can be read from an arbitrary terminal 407 that can be connected to the server.

While an example of three kinds of inspection apparatus and one review apparatus connected was shown above, at least one inspection apparatus and one review apparatus may be connected. Moreover, a plurality of various inspection apparatus and review apparatus may be provided. If each inspection apparatus has the same construction as in the second embodiment of the inspection apparatus according to the invention, the function of defect data analyzing apparatus can be achieved by any one of the inspection apparatus, and thus it is not necessary to separately provide the defect data analyzing apparatus.

While the above defect data analyzing method, and the inspection apparatus or review system having this method are provided to fundamentally process defect data of a single wafer, a plurality of wafers can be analyzed together as long as the defect distribution discrimination but not sampling is tried to make. In this case, first the defect position coordinates of a plurality of wafers are superimposed, and a high-density region image is generated on the basis of the superimposed defect position coordinates.

It should be further understood by those skilled in the art that the foregoing description has been made on embodiments of the invention and that various changes and modifications may be made in the invention without departing from the spirit of the invention and the scope of the appended claims.

What is claimed is:

1. A method of analyzing defect data obtained from inspection of defects of a semiconductor substrate in an apparatus for analyzing defect data, comprising:
   generating a defect distribution map using information of positions of defects of the semiconductor substrate detected by an inspection apparatus; and
   classifying said defects that exist on said generated defect distribution map into one of a plurality of defect categories including a congestion defect, a linear distribution defect, a ring/lump distribution defect and a random distribution defect through at least a discriminating step by using distance between adjacent defects and the local density of defects calculated from said defect distribution map.

2. A method of analyzing defect data according to claim 1, wherein, in the step of classifying, said ring/lump distribution defect is classified by grouping defects on said defect distribution map based on a distribution density of said defects and calculating a degree of coincidence between said grouped defects and a plurality of geometric patterns.

3. A method of analyzing defect data according to claim 2, wherein said geometric patterns include a ring pattern and a part of the ring pattern.

4. A method of analyzing defect data according to claim 1, wherein the distance between adjacent defects and the local density of defects are calculated by a Voronoi diagram which is generated based on position coordinates of said defects on said defects distribution map.

5. A method of analyzing defect data according to claim 4, wherein the random distribution defect is extracted after classification of the congestion defect, the linear distribution defect and the ring/lump defect.

6. A method of analyzing defect data according to claim 1, wherein the random distribution defect is extracted after classification of the congestion defect, the linear distribution defect and the ring/lump defect.

7. An apparatus for analyzing defect data, comprising:
   a first processor configured to generate a defect distribution map using information of positions of defects detected by an inspection apparatus; and
   a second processor configured to classify said defects that exist on said generated defect distribution map into one of a congestion defect, a linear distribution defect, a ring/lump distribution defect and a random distribution defect through at least a discriminating step by using, distance between adjacent defects and the local density of defects calculated from said defect distribution map generated by the first processor.

8. An apparatus for analyzing defect data according to claim 7, wherein said second processor is configured to classify said ring/lump distribution defect by grouping defects on said defect distribution map based on a distribution density of said defects and calculating a degree of coincidence between said grouped defects and a plurality of geometric patterns.

9. An apparatus for analyzing defect data according to claim 8, wherein said geometric patterns include a ring pattern and a part of the ring pattern.

10. An apparatus for analyzing defect data according to claim 7, wherein the distance between adjacent defects and the local density of defects are calculated by a Voronoi diagram which is generated based on position coordinates of said defects on said defect distribution map.

11. An apparatus of analyzing defect data according to claim 10, wherein the random distribution defect is extracted after classification of the congestion defect, the linear distribution defect and the ring/lump defect.

12. An apparatus of analyzing defect data according to claim 7, wherein the random distribution defect is extracted after classification of the congestion defect, the linear distribution defect and the ring/lump defect.

13. A method of analyzing defect data obtained from inspection of defects of a semiconductor substrate in an apparatus for analyzing defect data, comprising:
   generating a defect distribution map with positions of all defects by using position information of defects of the semiconductor substrate detected by an inspection apparatus;

calculating distance between adjacent defects and a Voronoi region area by using a closest point Voronoi diagram corresponding to said defect distribution map; and discriminating a congestion defect through at least a discriminating step using said distance between the adjacent defects;

discriminating a linear distribution defect through at least a discriminating step using said distance between the adjacent defects and said Voronoi region area;

discriminating a ring/lump distribution defect through at least a discriminating step using said distance between the adjacent defects and said Voronoi region area; and extracting another defect other than said congestion defect, said linear distribution defect and said ring/lump distribution defect.

14. A method of analyzing defect data according to claim 13, wherein said another defect is a random distribution defect.

15. A method of analyzing defect data according to claim 14, wherein the random distribution defect is extracted after classification of the congestion defect, the linear distribution defect and the ring/lump defect.

16. A method of analyzing defect data according to claim 13, including a step of classifying said ring/lump distribution defect by grouping defects on said defect distribution map based on a distribution density of said defects and calculating a degree of coincidence between said grouped defects and a plurality of geometric patterns.

17. A method of analyzing defect data according to claim 16, wherein said geometric patterns include a ring pattern and a part of the ring pattern.

18. An apparatus for analyzing defect data, comprising:

a defect distribution map generator configured to generate a defect distribution map with positions of all defects by using position information of defects detected by an inspection apparatus;

a calculator configured to calculate distances between adjacent defects and a Voronoi region area by using a closest point Voronoi diagram corresponding to said defect distribution map; and a processor configured to classify said defects by discriminating a congestion defect through at least a discriminating step using said distances between the adjacent defects, by discriminating a linear distribution defect through at least a discriminating step using said distance between the adjacent defects and said Voronoi region area, by discriminating a ring/lump distribution defect through at least a discriminating step using said distance between the adjacent defect and said Voronoi region area and by extracting another defect other than said congestion defect, said linear distribution defect and said ring/lump distribution defect.

19. An apparatus for analyzing defect data according to claim 18, wherein said another defect is a random distribution defect.

20. An apparatus of analyzing defect data according to claim 19, wherein the random distribution defect is extracted after classification of the congestion defect, the linear distribution defect and the ring/lump defect.

21. An apparatus for analyzing defect data according to claim 18, wherein said processor is configured to classify said ring/lump distribution defect by grouping defects on said defect distribution map based on a distribution density of said defects and calculating a degree of coincidence between said grouped defects and a plurality of geometric patterns.

22. An apparatus for analyzing defect data according to claim 21, wherein said geometric patterns include a ring pattern and a part of the ring pattern.

* * * * *

UNITED STATES PATENT AND TRADEMARK OFFICE
CERTIFICATE OF CORRECTION

| | | |
|---|---|---|
| PATENT NO. | : 8,086,422 B2 | Page 1 of 1 |
| APPLICATION NO. | : 12/341657 | |
| DATED | : December 27, 2011 | |
| INVENTOR(S) | : Shibuya et al. | |

It is certified that error appears in the above-identified patent and that said Letters Patent is hereby corrected as shown below:

Title Page, under Item (*) Notice: please delete "Subject to any disclaimer" and insert -- This patent is subject to a Terminal Disclaimer. --

Signed and Sealed this
Twenty-second Day of May, 2012

David J. Kappos
*Director of the United States Patent and Trademark Office*